(12) United States Patent  
Schauerte et al.

(10) Patent No.: US 6,690,971 B2
(45) Date of Patent: Feb. 10, 2004

(54) DEVICE FOR REGULATING HEART RATE AND HEART PUMPING FORCE

(75) Inventors: Patrick Schauerte, Herzogenrath (DE); Max Schaldach, deceased, late of Erlangen (DE); by Max Schaldach, Jr., legal representative, Berlin (DE)

(73) Assignee: Biotronik Mess - und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/726,501

(22) Filed: Nov. 30, 2000

(65) Prior Publication Data

US 2002/0026222 A1 Feb. 28, 2002

(30) Foreign Application Priority Data

Nov. 30, 1999  (DE) .......................... 199 57 649

(51) Int. Cl.$^7$ ............................................. A61N 1/365
(52) U.S. Cl. ................................. 607/17; 607/9
(58) Field of Search ......................... 607/2, 4–5, 9, 607/14, 17, 18, 23, 24, 115, 116, 118, 119, 122, 123

(56) References Cited

U.S. PATENT DOCUMENTS

| 4,865,036 | A | | 9/1989 | Chirife | |
| 5,199,428 | A | * | 4/1993 | Obel et al. .................. 600/516 |
| 5,203,326 | A | | 4/1993 | Collins | |
| 5,243,980 | A | | 9/1993 | Mehra | |
| 5,330,507 | A | * | 7/1994 | Schwartz .................... 600/510 |
| 5,522,854 | A | * | 6/1996 | Ideker et al. .............. 600/515 |
| 5,658,318 | A | * | 8/1997 | Stroetmann et al. ........... 607/6 |
| 5,700,282 | A | * | 12/1997 | Zabara ....................... 607/118 |
| 5,857,977 | A | | 1/1999 | Caswell | |
| 6,064,907 | A | | 5/2000 | Thong | |
| 6,073,048 | A | * | 6/2000 | Kieval et al. ................. 607/17 |

FOREIGN PATENT DOCUMENTS

| DE | 39 03 323 A1 | 12/1989 |
| DE | 196 09 365 A1 | 9/1997 |
| WO | WO 99/58191 A1 | 11/1999 |

* cited by examiner

*Primary Examiner*—Kennedy Schaetzle
*Assistant Examiner*—Kristen Droesch
(74) *Attorney, Agent, or Firm*—Hahn Loeser + Parks LLP; Stephen L. Grant

(57) ABSTRACT

A device for the therapy of supraventricular and ventricular bradycardial and tachycardial disrhythmias and/or for influencing the heart pumping force, including:

Figure 1:
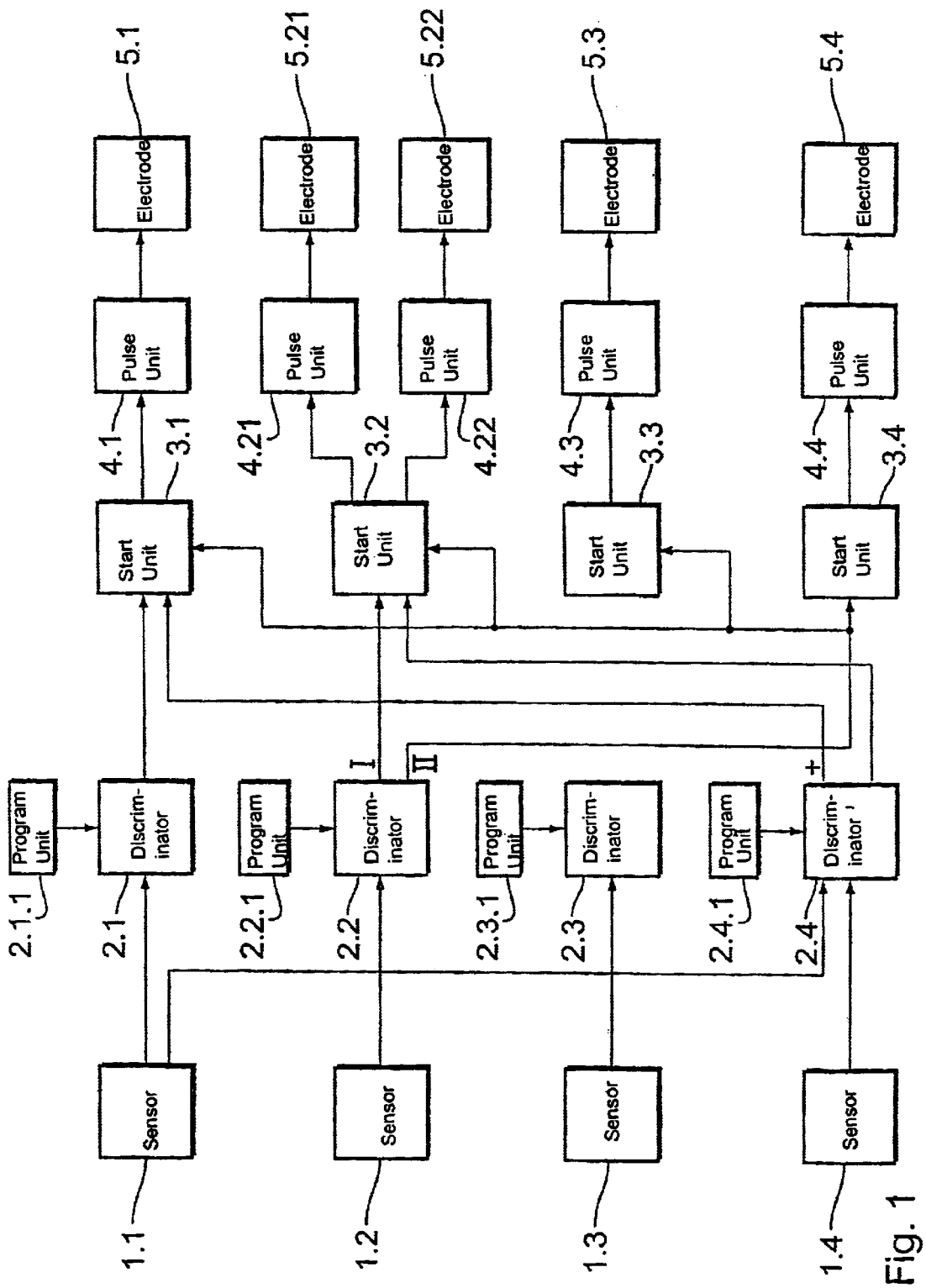

- electrodes for electrical and/or magnetic stimulation of parasympathetic nerves which innervate the sinus node, the atria, the atrioventricular node or the ventricles;
- electrodes for electrical and/or magnetic stimulation of the atria and ventricles and/or for ventricular cardioversion/defibrillation;
- a device for producing electrical and/or magnetic stimulation pulses which are passed to the electrodes; and
- a device for detecting the rate at which the human atria and ventricles beat, wherein said device measures atrial and ventricular contractions.

20 Claims, 5 Drawing Sheets

DEVICE FOR REGULATING HEART RATE AND HEART PUMPING FORCE

The invention concerns a device for the therapy of supraventricular and ventricular bradycardial and tachycardial disrhythmias and/or for influencing the heart pumping force.

The normal heart rate of a human being is between 60 and 100 beats per minute at rest while under a load it can rise to 180 beats per minute. A resting heart rate which is below 60 beats per minute is generally referred to as bradycardia while a resting heart rate which is over 100 beats per minute is referred to as tachycardia. Tachycardias can originate in the atria (so-called supraventricular tachycardias or atrial fibrillation) or can occur in the ventricles (so-called ventricular tachycardias and ventricular fibrillation). Bradycardias on the one hand can be the expression of a slowed rate of pulse production in the normal pacemaker center of the heart (the so-called sinus node) or can be caused by a pathological delay in transmission of the excitation from the atria to the ventricles (so-called AV-node disease). The by far most frequent supraventricular tachycardia, atrial fibrillation, occurs to an increasing extent with increasing age and is to be found in more than 5% of people who are over 65 years old. Supraventricular tachycardia results in particular by way of a reduction in the diastole time in a reduced degree of ventricular diastolic filling of the heart and thus a reduced heart time volume. Particularly in a situation involving pre-existing heart pumping weakness (so-called cardiac insufficiency), that results in arterial hypotonia (forward failure) and a back-up of blood in the lungs, which has an adverse effect on enrichment of the blood with oxygen in the lungs (so-called reverse failure). In addition the consumption of oxygen on the part of the heart rises with at the same time reduced diastolic coronary circulation.

Stimulation devices are known which influence the behaviour of the heart by stimulation and/or tachycardia termination or cardioversion. Those devices however exclusively have detection units and stimulation devices which in response to given input criteria trigger signals which act exclusively directly on the mechanical behaviour of the heart by stimulation of regions of the heart, on which the electrical activity signals which are directly related to contraction of the heart are propagated. That is disadvantageous because that means that signal events which are related to those signals that directly influence the cardiac events are not influenced.

The object of the present invention is to provide a device of the general kind set forth in the opening part of this specification, which is suitable for already involving regulating intervention in the preliminary stages of the known production of stimulation or defibrillation or cardioversion signals.

That object is attained by the features recited in claim 1.

The invention is based inter alia on the realisation that the frequency of supraventricular tachycardias can be reduced by activation of the parasympathetic autonomous nervous system and can be increased by activation of the sympathetic nervous system. The cardiac output can also be generally increased and/or reduced. A rate-increasing/decreasing action on the sinus node is referred to as a positively/negatively chronotropic action while an action which promotes/inhibits atrioventricular conduction (AV-conduction) is referred to as a positively/negatively dromotropic action.

Parasympathetic nerve fibers which innervate the sinus node, the atria and the atrioventricular nodes extend along the superior vena cava, the coronary sinus and the right pulmonary artery. Sympathetic nerve fibers which result in a rise in the sinus node and/or atrium rate and an acceleration of atrioventricular conduction extend to the stellatum ganglion by way of a dorsal nerve loop which bears from the back against the arteria subclavia (the so-called dorsal ansa subclavia) and a ventral nerve loop which bears from the front against the arteria subclavia (so-called ventrale ansa subclavia) to the cardiac muscle. The ansae subclaviae contain virtually all sympathetic nerve fibers which lead from the ganglion stellatum to the cardiac muscle. These predominantly involve pre-ganglionary nerve fibers which are changed over to post-ganglionary fibers in the ganglion cerviclae medius and the upper thoracal boundary line ganglia.

Ventricular tachycardias have similar hemodynamic changes to supraventricular tachycardias. As however in contrast to many supraventricular tachycardias a synchronised atrial contraction prior to the ventricle contraction does not occur, a ventricular tachycardia, at the same rate, is hemodynamically worse than a supraventricular tachycardia. In particular however the altered intraventricular contraction process in the situations involving ventricular tachycardia results in a marked reduction in beat volume and arterial hypotonia, which means that patients with ventricular tachycardia generally lose consciousness more quickly than patients with a supraventricular tachycardia at the same rate. In particular however ventricular tachycardias quickly degenerate into ventricular fibrillation, a condition in which the ventricles beat asynchronously and incompletely at frequencies>400 beats per minute. That results in a loss in arterial blood pressure. Ventricular tachycardias and ventricular fibrillation are the main cause of so-called sudden heart death which is responsible for about 80% cardiac-related deaths per annum.

The sympathetic autonomous nervous system plays a key role in the occurrence of ventricular tachycardias and ventricular fibrillation. Thus the sympathetic neurotransmitters adrenaline and noradrenaline can trigger abnormal automaticity and ventricular extrasystoles in the infarct area or can accelerate the transmission speed through myocardium scars after a cardiac infarction, which promotes the occurrence of ventricular orbits and ventricular tachycardias.

Finally, patients after cardiac infarctions are frequently found to have areas in the cardiac muscle in which the sympathetic cardiac nerves have also perished, which causes denervation oversensitivity of those areas to adrenaline and noradrenaline. Such an oversensitivity and non-homogeneous sympathetic innervation promote the occurrence of ventricular tachycardias and ventricular fibrillation.

The parasympathetic autonomous nervous system and its neurotransmitter acetyl choline antagonise the influence of the sympathetic nervous system on the heart and can prevent sudden heart death in animal models.

Clinical testing procedures which measure the sympathetic and parasympathetic tone in patients have shown that an increased sympathetic tone and reduced parasympathetic tone significantly promote the occurrence of sudden heart death.

Parasympathetic nerve fibers which innervate the ventricles accumulate in a fat clump at the level of the coronary sinus in the region of the proximal left-hand coronary artery.

The second essential parameter having an influence on the heart time volume, besides the heart rate, is the contraction force of the heart. It describes what amount of blood is expelled per heart beat (beat volume). In addition it determines the extent and the rate of the rise in pressure in the artery upon a heartbeat. Numerous diseases which can result in a decline in heart musculature such as for example coronary heart disease with cardiac infarctions can result in a reduction in the pumping force of the heart. The result of this is that, at a normal heart rate, the pumping force of the cardiac muscle is not sufficient to permit a minimally necessary beat volume for the purposes of maintaining normal arterial blood pressure and for the purposes of preventing an accumulation of blood upstream of the heart. Influencing parameters which result in an increase in the contraction force of the heart are referred to as positively inotropic parameters. Positively inotropic actions are afforded in particular by catecholamines such as adrenaline and noradrenaline which are diffused by the so-called sympathetic autonomous nervous system as neurotransmitters.

Sympathetic nerve fibers which innervate the ventricles extend in a ventral and dorsal nerve loop around the right and left arteria subclavia. Further sympathetic nerve fibers run in a ventrolateral nerve from the stellatum ganglion and the inferior cervical boundary strand ganglion respectively along the pulmonary vein and the coronary sinus to the ventricles.

In accordance with the invention, including advantageous developments, there is provided a medical electrostimulation device for the therapy of supraventricular and ventricular bradycardial and tachycardial disrhythmias and for increasing the heart pumping force, comprising electrodes for the electrical and/or magnetic stimulation of parasympathetic nerves which innervate the sinus node, the atria, the atrioventricular nodes or the ventricles;

electrodes for the electrical and/or magnetic stimulation of the atria and ventricles and for ventricular cardioversion/defibrillation;

a device for producing electrical and/or magnetic stimulation pulses which are passed to the electrodes;

a device for detecting the rate at which the human atria and ventricles beat, said device measuring atrial and ventricular depolarisations;

a device for detecting biological parameters such as the arterial blood pressure, the right-ventricular or left-ventricular pressure, oxygen saturation of the blood or the heart time volume, the myocardial or thoracal impedance or monophase action potentials or evoked myocardial potentials;

a device for programming a frequency limit above or below which a beat rate of the heart is identified as tachycardia or bradycardia;

a device for programming a blood pressure/heart time volume limit, below which a heart insufficiency requiring treatment is identified;

a device for programming a blood pressure/heart time volume, above which sympathetic nerve stimulation in inhibited or reduced;

a start unit which reacts to the detection unit and which activates the device producing the stimulation pulses, if the detected heart beat rate of the atria or ventricles exceeds/falls below the programmed frequency limit;

a start unit which reacts to the detection unit and which activates the device producing the stimulation pulses when the arterial blood pressure/heart time volume falls below a programmed lower limit;

the stimulation pulses can be delivered over a defined period of time continuously or as short bursts. Stimulation bursts in turn can be delivered either asynchronously or in synchronised relationship with the atrial or ventricular depolarisation. Synchronisation is then effected with a varying time delay in relation to the measured atrial/ventricular depolarisation in the atrial/ventricular refractory time;

a unit which compares the atrium/ventricle frequency measured during stimulation by the detection units and the arterial blood pressure and the heart time volume to the corresponding values prior to/without stimulation and the corresponding programmed limit values; and a stimulation unit which can provide for atrial and/or ventricular electrical and/or magnetic myocardial stimulation or cardioversion/defibrillation.

For electrical and/or magnetic stimulation of parasympathetic nerve fibers which are to reduce the atrium frequency in the event of supraventricular tachycardias and/or which are intended to slow down the ventricle frequency in the event of supraventricular tachycardias electrodes are implanted in the superior vena cava, the inferior vena cava, in the right atrium, in the coronary sinus, in both jugular veins, the right or left vena anonyma or the pulmonary artery.

Electrodes are implanted in the coronary sinus for electrical and/or magnetic stimulation of parasympathetic nerve fibers which are to prevent or terminate ventricular tachycardias/ventricular fibrillation.

For electrical and/or magnetic stimulation of parasympathetic nerve fibers which innervate the sinus nodes, electrodes are implanted in the jugular veins, the superior vena cava, the lateral right atrium in the region of the intersection of the pulmonary veins or in the pulmonary arteries.

For electrical and/or magnetic stimulation of sympathetic nerve fibers which are to increase the heart rate or the pumping force of the heart, electrodes are implanted in the right and/or left arteria subclavia or vena subclavia or the pulmonary veins or the coronary sinus.

The stimulation electrodes can be fixed intravascularly or extravascularly/epicardially at the identified stimulation locations. Nerve stimulation can be effected in a unipolar or bipolar mode, in which case the bipolar reference electrode can be part of the nerve stimulation electrode or part of a second nerve stimulation electrode implanted in the proximity of the first nerve stimulation electrode. In that respect fixing of the probes can be effected actively, for example by screw mechanisms or passively, for example by anchoring devices.

The pulse-producing device for the stimulation of autonomous nerves and for electrical and/or magnetic myocardial stimulation can involve any suitable technology for the production of stimulation pulses at a frequency of between 0 and 100 Hz and a single pulse duration of between 0 and 10 ms. The pulses can be monophase or biphase.

By virtue of a modification in the pulse-producing unit, instead of or in addition to electrical pulses, it is also possible to produce alternating magnetic fields in the pico to $\mu$-tesla range, which are delivered to the nerves and/or the myocardium by way of suitable electrodes which involve appropriate coil structures.

Nerve stimulation is typically implemented at 20 Hz with a pulse duration of between 0.1 and 4 ms.

When the situation involves ventricular tachycardia, short bursts (typically between 10 and 50 ms in duration) of high-frequency individual pulses are delivered immediately after ventricular depolarisation (R-blip) in order to avoid ventricular myocardial depolarisation during stimulation of the parasympathetic nerves along the coronary sinus. Likewise stimulation of the ventrolateral nerve which extends close to the atrial/ventricular myocardium is preferably effected in bursts (typically between 10 and 50 ms in duration) of high-frequency individual pulses which are delivered immediately after ventricular depolarisation (R-blip) in order to prevent ventricular myocardial depolarisation during nerve stimulation.

The electrodes for detection of the atrial/ventricular frequency are disposed in the atrium/ventricle and are connected to an adjustable signal amplifier which amplifies the detected signal to varying degrees, depending on the respective signal magnitude. The band pass properties of the filter of that amplifier are optimised for the detection of atrium/ventricle depolarisations. The mode of operation of the amplifier/filter can correspond to that of known atrium/ventricle pacemakers.

With the measures according to the invention, it is possible to indirectly influence the heart rate by comparison of the current heart rate with one by way of a physiological parameter (activity parameter) for the heart output requirement by sympathetic or parasympathetic stimulation— depending on whether the current heart output is just exceeding or is below the current requirement. That occurs in contrast to previous rate-controlled pacemakers in which the desired stimulation rate was set by direct stimulation of the heart muscle at the corresponding rate.

Figure 2:
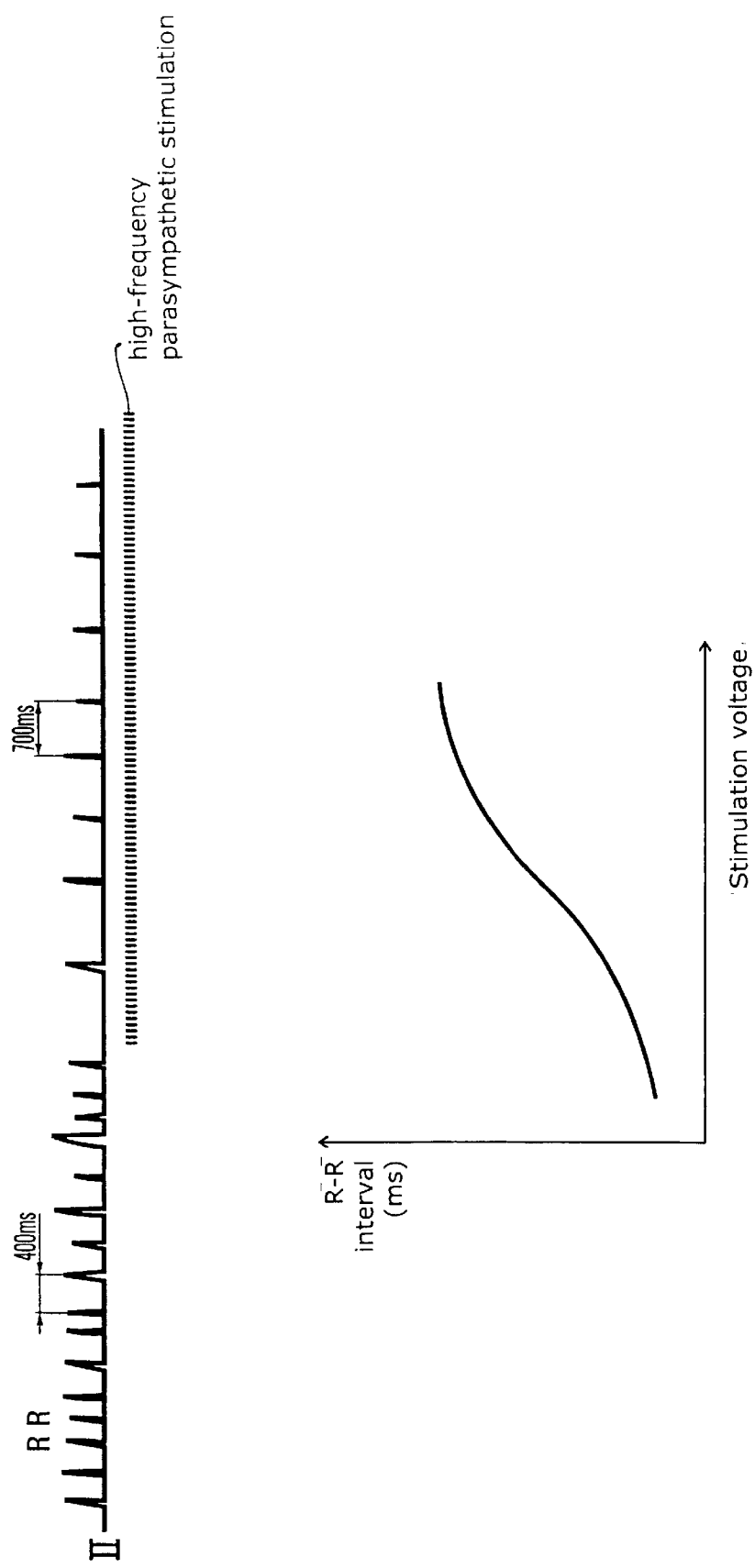
Figure 3:
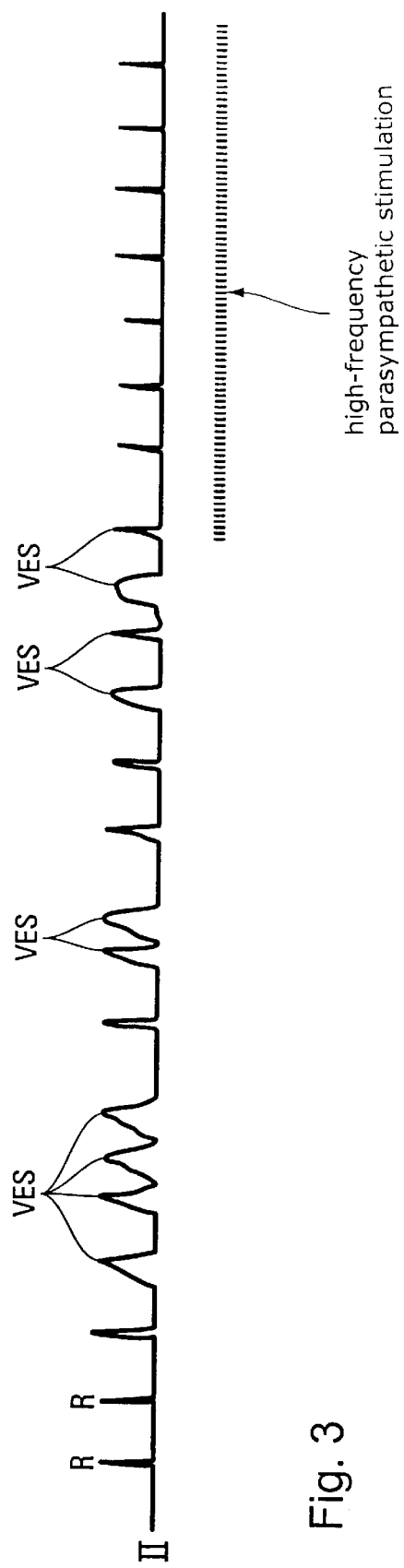
Figure 4:
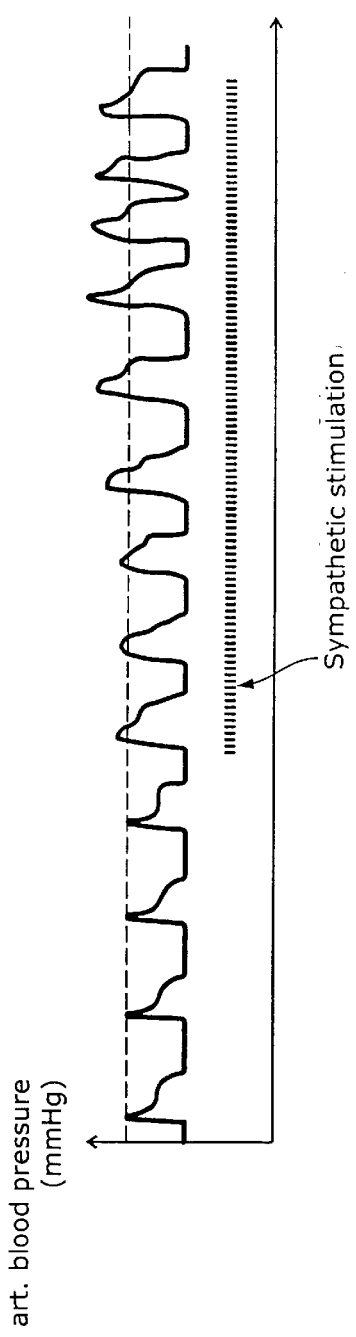
Figure 5:
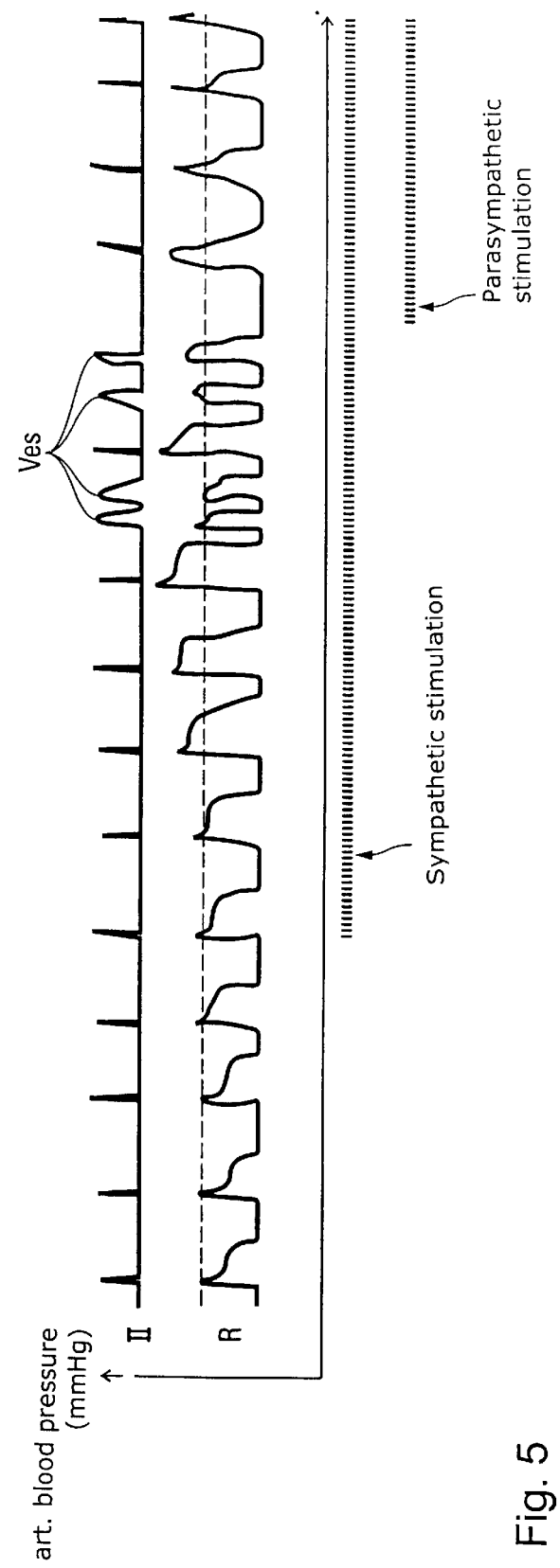
Figure 6:
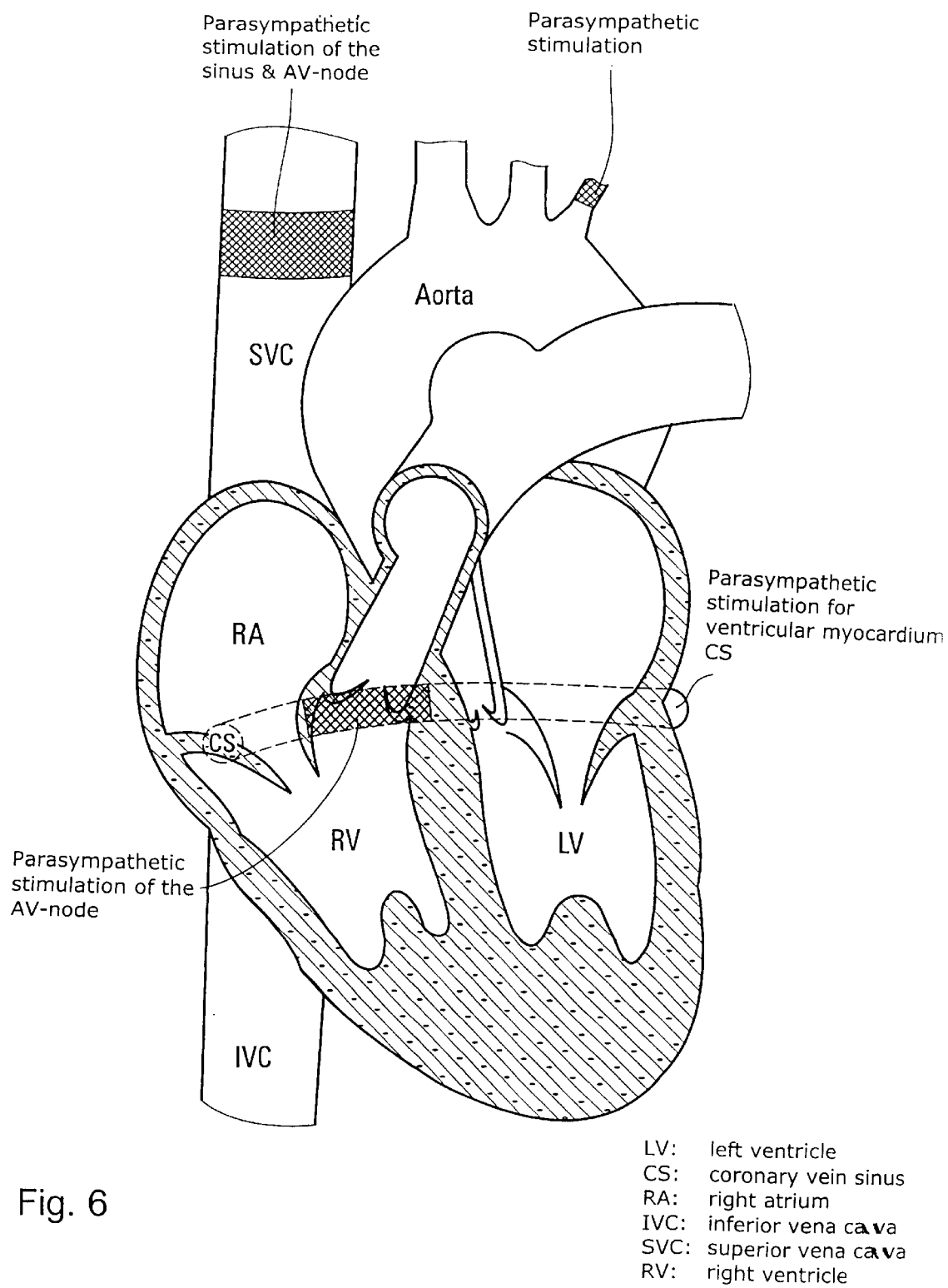

Other advantageous developments are characterised in the appendant claims. An advantageous embodiment of the invention is described in greater detail hereinafter with reference to the drawings in which:

FIG. 1 shows an embodiment of an advantageous stimulation device in the form of a block circuit diagram, FIG. 2 shows a time diagram as an example in respect of parasympathetic stimulation in the superior vena cava for reducing the atrial frequency in the event of supraventricular tachycardias, FIG. 3 shows a time diagram as an example of parasympathetic stimulation in the coronary sinus or the right and/or left arteria/vena jugularis for the termination/prevention of ventricular tachycardias, FIG. 4 shows a further time diagram as an example of sympathetic stimulation in the left arteria subclavia, FIG. 5 shows a further time diagram as an example of sympathetic stimulation of the ansa subclavia for preventing a neurocardiogenic syncope, and FIG. 6 is a diagrammatic overview of the mounting locations of the said electrodes in a sectional view of the heart.

The block circuit diagram shown in FIG. 1 diagrammatically illustrates an advantageous embodiment by way of example. Shown in succession in the horizontal direction are the detection units comprising sensor portions 1.x and discriminator portions 2.x, and actuation of a start unit 3.x for activation of the corresponding pulse-producing unit 4.x by way of downstream-connected electrodes 5.x. A programming unit 2.x.1 serves in each case for presetting limit values at which the respective start units respond.

The lines refer in their left-hand part to the detected signals and in their right-hand part to the stimulation measures to be initiated and the corresponding electrodes as well as the associated start and stimulation units.

The first line x.1 relates to the elimination of heart insufficiency by sympathetic stimulation with the corresponding detection of a heart output by the sensor 1.1 and comparison with a pre-programmed limit value.

The second line x.2 involves rate detection (AV) in regard to cardiac activity without stimulation. In that way, in response to tachycardia identification, depending on the nature of the tachycardia (supraventricular, ventricular), parasympathetic stimulation is implemented by way of different pulse-producing units 4.21 and 4.22 in different regions by way of suitably arranged electrodes 5.21 and 5.22 respectively. The discriminator portion 2.2 also records the last heart rate in the non-stimulated mode of operation for comparison with the result in a situation involving subsequent parasympathetic or sympathetic stimulation, for the purposes of monitoring the outcome.

The third line involves implementation of the usual bradycardia identification in the context of normal pacemaker therapy, with escape intervals, and corresponding control of the electrodes disposed in the atrium and/or auricle, in conventional pacemaker technology.

In the fourth line, a reference value in respect of the current heart output requirement is ascertained by way of a physiological sensor parameter by the sensor 1.4. This may involve any parameter which was used hitherto in relation to rate-controlled pacemakers for influencing the heart rate. By comparison with the output parameter of the sensor 1.1 for heart output and a pre-programmed dependency up to limit values which are also pre-programmed (the reference or target function of the heart rate in dependence on the heart output requirement) sympathetic stimulation is initiated in the event of excessively slight cardiac activity (blocks 4.1, 5.1), while in the case of excessively great cardiac activity parasympathetic stimulation is initiated (blocks 4.21, 5.21 and 4.22, 5.22 respectively). That for the first time permits genuine 'regulation' of the heart rate by indirect stimulation.

For the avoidance of repetition, for signal allocations and definitions attention is directed to the remainder of the description and the claims.

FIG. 2 shows an example of parasympathetic stimulation in the superior vena cava for reducing the atrium frequency in the event of supraventricular tachycardias and reducing the ventricle frequency in the event of atrial fibrillation. If the atrium frequency (ventricle frequency in the case of atrial fibrillation) exceeds a programmed upper limit frequency, a burst of high-frequency electrical and/or magnetic pulses (typically 20 Hz, pulse duration 2 ms, pulse voltage between 5 and 20 V) is initiated by way of the start unit. Those pulses are delivered by way of the nerve stimulation electrode positioned in/at the superior vena cava. During parasympathetic stimulation, the atrium frequency/ventricle frequency during parasympathetic stimulation is compared by a comparison unit with the programmed upper frequency limit. If the initial nerve stimulation intensity is not below that upper frequency limit, the nerve stimulation intensity is increased stepwise until the atrium/ventricle frequency falls below the programmed upper limit frequency. If the intensity falls below the upper limit frequency during parasympathetic stimulation the level of nerve stimulation intensity is automatically lowered. The upper limit of atrium/ventricle frequency in a situation involving atrial tachycardia/atrial fibrillation can automatically be adapted to the physical activity of the patient. Sensors for measuring the physical activity can correspond to those of known atrium/ventricle pacemakers.

If during parasympathetic stimulation in the superior vena cava there is a drop in the heart time volume/arterial blood pressure below a fixed limit value, the level of parasympathetic stimulation intensity in the superior vena cava is reduced until the lower limit value in respect of the heart time volume/arterial blood pressure is exceeded again.

FIG. 3 shows an example of parasympathetic stimulation in the coronary sinus or the right and/or left arteria/vena jugularis for terminating/preventing ventricular tachycardias. The occurrence of large numbers of ventricular extrasystoles or non-continuous ventricular bursts (duration<10 seconds) triggers, by way of the start unit, a burst of high-frequency electrical and/or magnetic pulses (typically 20 Hz, pulse duration 2 ms, pulse voltage between 5 and 20 V). Those pulses are delivered by way of the nerve stimulation electrodes which are positioned in/at the coronary sinus. The number and prematurity of the ventricular extrasystoles or the cycle length of the non-continuous ventricular tachycardias which trigger off parasympathetic stimulation can be freely programmed. During parasympathetic stimulation the ventricle frequency and the occurrence of ventricular extrasystoles and non-continuous ventricular bursts during parasympathetic stimulation is compared by a comparison unit to the programmed limit values. If the value rises above/falls below the programmed limit values during parasympathetic stimulation, the nerve stimulation intensity is raised/reduced stepwise until the value falls below the programmed limit values of the ventricular extrasystoles/non-continuous ventricular tachycardias.

If during parasympathetic stimulation in the coronary sinus/vena/arteria jugularis there is a drop in the heart time volume/arterial blood pressure below a fixed limit value, the level of parasympathetic stimulation intensity in the coronary vein sinus is reduced until the lower limit value in respect of heart time volume/arterial blood pressure is again exceeded.

In the case of ventricular tachycardia parasympathetic stimulation is effected in the coronary sinus/vena jugularis interna/externa, wherein the stimulation bursts are delivered in synchronised relationship to the R-blips in the ventricular refractory time in order to avoid ventricular myocardial stimulation. The diagnosis of ventricular tachycardia is based on two criteria: the ventricle frequency exceeds a fixed limit frequency and there is no drop in the ventricle frequency during parasympathetic stimulation effected as a trial, in the superior vena cava. If, in a situation involving parasympathetic stimulation, termination of the ventricular tachycardia does not occur, a ventricular anti-tachycardial overstimulation attempt or cardioversion is initiated. Prior to and during cardioversion/defibrillation parasympathetic stimulation is continued in the coronary vein sinus or the right and/or left vena jugularis interna. That makes it possible to reduce the amount of energy which is required for ventricular cardioversion. Upon defibrillation of ventricle fibrillation, parasympathetic stimulation, stimulation in the coronary vein sinus or the right and/or left vena jugularis interna can also be initiated in order to reduce the ventricular defibrillation threshold. Similarly, parasympathetic stimulation can also be delivered in the right/left vena/arteria jugularis, the superior vena cava, the coronary vein sinus or the pulmonary artery immediately prior to and during cardioversion of atrial fibrillation in order to reduce the atrial cardioversion threshold.

FIG. 4 shows an example of sympathetic stimulation in the left arteria subclavia. If the arterial blood pressure/heart time volume falls below a programmed limit value, sympathetic stimulation is implemented until that limit value is exceeded. If the atrium frequency or ventricle frequency in sympathetic stimulation exceeds a programmed upper limit value, the level of stimulation intensity is reduced until the heart rate falls below that limit value. In that case the level of sympathetic stimulation intensity is reduced only to such an extent that the arterial blood pressure/heart time volume remains above the corresponding programmed limit value. If during the reduction in sympathetic nerve stimulation intensity the arterial blood pressure/heart time value should fall below the corresponding limit value, there is again an increase in the level of sympathetic stimulation intensity. At the same time the start unit initiates parasympathetic stimulation in the superior vena cava until the atrium frequency/ventricle frequency of the jugular veins falls below the corresponding limit frequency.

FIG. 6 is a diagrammatic overview of the mounting locations of the specified electrodes in the region of the heart. This involves a diagrammatic view in section.

If during sympathetic stimulation large numbers of ventricular extrasystoles are triggered off, the level of sympathetic stimulation intensity is reduced to such an extent that the arterial blood pressure/heart time volume remains above the corresponding programmed limit value. If the ventricular extrasystoles persist, initiation of a parasympathetic stimulation is effected in the coronary sinus, the jugular veins or the superior venae cavae until the ventricular extrasystoles/non-continuous tachycardias fall below a programmed limit value. The level of intensity of parasympathetic stimulation in the coronary sinus is increased only to such an extent that this does not result in the arterial blood pressure/heart time volume falling below the programmed limit value.

FIG. 5 illustrates an example of sympathetic stimulation of the ansa subclavia for preventing a neurocardiogenic syncope. Typically the device is activated by the patient at the beginning of a dizziness/presyncope symptom triggered by arterial hypotonia and/or bradycardia and inactivated after an improvement in the symptoms. Provision is also made however for automatic sympathetic stimulation in the event of a drop in the heart rate and/or the arterial blood pressure below a programmed limit value.

The pulse-producing unit can comprise an implantable generator which is in direct electrical and/or magnetic contact with the stimulation and sensor electrodes. In addition however the pulse-producing unit may involve an external generator which is applied to the surface of the body from the exterior and which can produce a stimulation voltage at the electrodes, without having direct electrical and/or magnetic connection with the stimulation and measurement electrodes, for example inductively.

The unit for regulating the heart rate and the heart pumping force incorporates in its typical design configuration an anti-bradycardial ventricular pacemaker and an anti-tachycardial ventricular implantable defibrillator. That permits anti-bradycardial safety stimulation if under parasympathetic stimulation there is an unwantedly great drop in heart rate. If during sympathetic stimulation induction of a ventricular tachycardia or ventricular fibrillation should occur, there is also defibrillation protection.

In specifically modified units however it is also possible to implement the possibility of electrical atrial stimulation or defibrillation/cardioversion.

Although the described invention relates to a device which can simultaneously implement autonomous nerve stimulation at all described stimulation locations, the present invention also addresses devices which serve only one of the described nerve stimulation processes. In principle a device can implement each of the various neurostimulation processes solely or in combination with other neurostimulation processes. The number of sensors for the heart rate or other biological parameters can also vary. Finally, the invention also addresses the combination of the neurostimulator with a plurality of conventional, anti-bradycardial and/or anti-tachycardial pacemaker types/defibrillators.

What is claimed is:

1. A device for the therapy of supraventricular and ventricular bradycardial and tachycardial disrhythmias and for influencing the heart pumping force, comprising:

electrodes for stimulating, by at least one of an electrical and a magnetic pulse, at least one of the sympathetic and parasympathetic nerves which innervate the sinus node, the atria, the atrioventricular node or the ventricles, with an associated first and second means for producing stimulation pulses which are at least one of electrical and magnetic in nature and which are passed to the corresponding electrodes, wherein said first and second pulse-producing means are activated respectively by an associated first and second means for detecting a first and second input signal when said first and second input signal correspond to a predetermined criterion, and electrodes for stimulating, by at least one of electrical and magnetic stimulation of the atria and ventricles and for ventricular cardioversion/defibrillation with an associated third and fourth means for producing stimulation pulses which are at least one of electrical and magnetic in nature and which are passed to said electrodes, wherein said third and fourth pulse-producing means are activated respectively by an associated third and fourth means for detecting a third and fourth input signal when said third and fourth input signal correspond to a predetermined criterion.

2. The device of claim 1 further comprising a means for detecting at least one biological parameter selected from a group consisting of: arterial blood pressure, the right or left ventricular pressure, oxygen saturation of the blood and the heart time volume.

3. The device of claim 2 further comprising a means for programming at least one of a blood pressure and heart time volume limit, below which a heart insufficiency in need of treatment is identified.

4. The device of claim 3 further comprising a means for activating the corresponding stimulation pulse-producing means in response to the detecting means when the arterial blood pressure and/or the heart time volume falls below a programmed lower limit.

5. The device of claim 1 further comprising a means for programming a regulating relationship which is a measurement in respect of the intensity of the sympathetic or parasympathetic stimulation to be initiated in dependence on the intensity of a parameter forming a measurement in respect of the current heart output requirement.

6. The device of claim 5 further comprising a means for programming limits above or below which a physiological parameter produces a sympathetic or parasympathetic stimulation effect.

7. The device of claim 1 further comprising a stimulation device for myocardial stimulation, electrically or magnetically, by stimulation of at least one of an atrium or a ventricle.

8. The device as set forth in claim 1 further comprising a means for detecting the rate at which the human atria and ventricles beat by measuring atrial and ventricular contractions.

9. The device of claim 8 further comprising a means for programming frequency limits above or below which a beat rate of the heart is identified as tachycardia or bradycardia.

10. The device of claim 9 further comprising a means for activating the corresponding stimulation pulse-producing means in response to the detecting means when the detected heartbeat rate of the atria or ventricles exceeds/falls below the respective programmed frequency limit.

11. The device of claim 8 further comprising a means for detecting at least one biological parameter selected from a group consisting of: arterial blood pressure, the right or left ventricular pressure, oxygen saturation of the blood and the heart time volume.

12. The device of claim 11 further comprising a means for programming frequency limits above or below which a beat rate of the heart is identified as tachycardia or bradycardia.

13. The device of claim 12 further comprising a means for programming at least one of a blood pressure and heart time volume limit, below which a heart insufficiency in need of treatment is identified.

14. The device of claim 13 further comprising a means for programming a regulating relationship which is a measurement in respect of the intensity of the sympathetic or parasympathetic stimulation to be initiated in dependence on the intensity of a parameter forming a measurement in respect of the current heart output requirement.

15. The device or claim 14 further comprising a means for programming limits above or below which a physiological parameter produces a sympathetic or parasympathetic stimulation effect.

16. The device of claim 15 further comprising a means for activating the corresponding stimulation pulse-producing means in response to the detecting means when the detected heartbeat rate of the atria or ventricles exceeds/falls below the respective programmed frequency limit.

17. The device of claim 16 further comprising a means for activating the corresponding stimulation pulse-producing means in response to the detecting means when the arterial blood pressure and/or the heart time volume falls below a programmed lower limit.

18. The device of claim 17 further comprising a means for comparing the frequency of at least one of the atria and the ventricles measured during stimulation by the detecting means and at least one of the arterial blood pressure and the heart time volume to at least one of the corresponding values prior to stimulation and the corresponding programmed limit values.

19. The device of claim 18 further comprising a stimulation device for myocardial stimulation, electrically or magnetically, by stimulation of a least one of an atrium or a ventricle.

20. A device for the therapy of supraventricular and ventricular bradycardial and tachycardial disrhythmias and for influencing the pumping force of a heart of a subject, said device comprising:

a first and a second electrode for stimulating at least one of the sympathetic and parasympathetic nerves which innervate the sinus node, the atria, the atrioventricular node or the ventricles, the first and second electrodes being adapted for intraluminal placement in the subject;

a first and a second means for producing stimulation pulses, associated with the corresponding electrodes and adapted to pass the pulses thereto;

a first and a second means for detecting a first and second input signal when said first and second input signal correspond to a predetermined criterion, the first and second detecting means associated with the corresponding pulse-producing means for activating the corresponding pulse-producing means when the first and second input signals correspond to a predetermined criterion;

a third and a fourth electrode for stimulating the atria and ventricles and for ventricular cardioversion/defibrillation; the third and fourth electrodes being adapted for intraluminal placement in the subject;

a third and a fourth means for producing stimulation pulses, associated with the corresponding electrodes and adapted to pass the pulses thereto;

a third and a fourth means for detecting a third and a fourth input signal the rust and second detecting means associated with the corresponding pulse-producing means for activating the corresponding pulse-producing means when the third and fourth input signals correspond to a predetermined criterion.

* * * * *